United States Patent [19]

Batorewicz

[11] 3,932,565

[45] Jan. 13, 1976

[54] POLYMERIC BROMINE-CONTAINING PHOSPHORAMIDATE POLYOLS

[75] Inventor: Wadim Batorewicz, New Haven, Conn.

[73] Assignee: Uniroyal Inc., New York, N.Y.

[22] Filed: Dec. 26, 1973

[21] Appl. No.: 430,995

[52] U.S. Cl. ... 260/928; 260/2.5 AR; 260/77.5 AR; 260/239 A; 260/239 EP; 260/247.7 D; 260/268; 260/927 R; 260/929; 260/986
[51] Int. Cl.² ................ C07F 9/24; C08G 18/83
[58] Field of Search ............................ 260/928, 929

[56] References Cited
UNITED STATES PATENTS

| | | | |
|---|---|---|---|
| 3,192,242 | 6/1965 | Birum | 260/986 |
| 3,228,998 | 1/1966 | Fierze et al. | 260/928 |
| 3,256,249 | 6/1966 | Vogt et al. | 260/928 X |
| 3,578,731 | 5/1971 | Mange et al. | 260/928 X |

*Primary Examiner*—Anton H. Sutto
*Attorney, Agent, or Firm*—Willard R. Sprowls, Esq.

[57] ABSTRACT

Polymeric bromine-containing phosphoramidate polyols are obtained by reacting bromine with spirocyclic phosphoramidites and thereafter reacting the brominated products with a polyol, in the presence of an acid acceptor. The novel viscous polymers thus produced react with polyisocyanates to produce polyurethanes. Polyurethanes so made are characterized by improved flame-retardant properties compared with conventional polyurethanes.

4 Claims, No Drawings

POLYMERIC BROMINE-CONTAINING PHOSPHORAMIDATE POLYOLS

BACKGROUND OF THE INVENTION

1. Field of the Invention

The field of the invention is novel polymeric bromine-containing phosphoramidate polyols novel intermediates and methods for use in synthesizing such novel polyols and use thereof as co-reactive flame retardants in the preparation of polyurethanes.

2. Background of the Invention

Incorporation of phosphorus or halogen compounds to impart flame resistance to an organic resin is well known in the art. It is also well known in the art that incorporation of both phosphorus and halogen into the polymer produces a synergistic effect, and furthermore, that bromine compounds are more effective flame reducing agents than the corresponding chlorine analogs.

Numerous phosphorus and halogen compositions have been disclosed as flame retardants for organic resins. These are of two general types: additive and reactive flame retardants. The reactive type flame retardants are those which possess at least two reactive sites through which they are chemically bound to the polymer backbone. These are usually superior to the additive type flame retardants, for they will not leach out, evaporate or sublime out of the polymer substrate during processing or use, thus leaving the polymer surface unprotected and often badly degraded.

Simple phosphoramidates have been disclosed and claimed as flame retardants. Thus U.S Pat. No. 2,971,929 issued Feb. 14, 1961 in the name of Glade discloses monomers of the type:

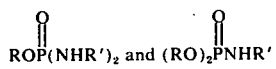

as flame retardants for textile materials. Also, British Pat. Nos. 835,581 and 585,582 disclose

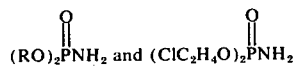

type structures as useful flame retardants for textiles.

German Patent 1,163,018 discloses bis(2-chloroethoxy)-phosphoramide,

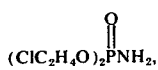

as a flame retardant for polyurethanes.

All of the above are simple monomeric molecules which are additive type materials. They, therefore, completely differ in substance and scope from the materials of this invention.

On the other hand, U.S. Pat. Nos. 3,256,249 and 3,335,129 issued in the name of Vogt et al on June 14, 1966 and Aug. 8, 1967, respectively, disclose certain phosphoramidate polyols as reactive flame retardants for polyurethane resins. These are prepared by treating polyols with amidophosphorochloridates according to the equations:

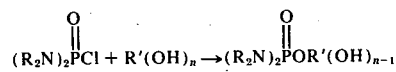

and

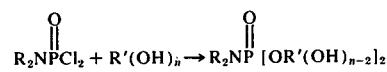

These phosphoramide polyols are derived from different starting materials and, therefore, are quite different chemically from the compositions of my invention. Just as important, these do not contain bromine atoms and therefore are inferior in activity to the compounds of the present invention.

U.S. Pat. Nos. 3,597,503 granted on Aug. 3, 1971 in the name of Wilson et al discloses monomeric cyclic phosphoroamidates which are made by reacting a diol with a phosphoryl trihalide to form a product, reacting this product with ammonia or a primary or secondary amine to form a second product, and subsequently reacting this second product with an aldehyde or an epoxide. The final products are said to be reactive flame retardants for polyurethanes. None of the products disclosed in this patent remotely resembles the polymeric bromide-containing phosphoroamidate polyols of the present invention.

SUMMARY OF THE INVENTION

The invention is a new class of polymeric bromine-containing phosphoramidate polyols having the general formula III below, processes of preparing these polymeric materials, and their use as reactive flame retardants in the preparation of polyurethanes.

The polymeric bromine-containing phosphoramidate polyols of this invention are reactive type flame retardants, containing active hydroxyl groups capable of forming urethane type linkages with isocyanates and thus being chemically bound to the polyurethane resin or elastomer. They are prepared in accordance with the present invention by brominating a spirocyclic phosphoramidite, having the general formula I below, at low temperature, and causing addition of the resulting intermediate having the general formula II below to a diol in the presence of an acid acceptor (for the hydrobromic acid which is split off) such as a tertiary amine to form the novel phosphoramidate diol products having the general formula III.

The phosphoramidate polyols of this invention are prepared according to the following equations:

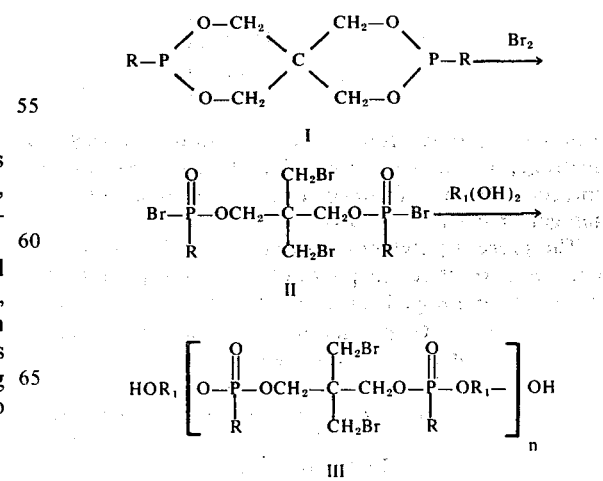

The novel compositions of this invention have the general formulas II and III wherein R is a radical selected from a group consisting of radicals having the formulas:

(a) 

wherein $R_2$ and $R_3$ can be the same or different and denote an alkyl radical having from 1 to 6 carbon atoms, or an aralkyl or an alkaryl radical, or substituted aralkyl or alkaryl radical, all of the latter having from 7 to 12 carbon atoms, (b) 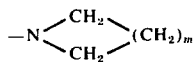

wherein $m$ is zero or an integer of from one to three, (c) 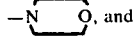, and (d) 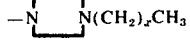

wherein $x$ is zero or an integer of from one to five; wherein $R_1$ is a radical selected from the following group:
e. alkylene radicals or halogen substituted alkylene radicals, both having from 2 to 10 carbon atoms,
f. alkenylene radicals having from 4 to 10 carbon atoms,
g. alkynylene radicals having from 4 to 10 carbon atoms, and
h. radicals having the formula

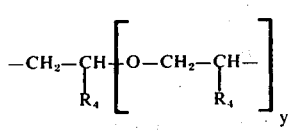

wherein $R_4$ is selected from the group consisting of hydrogen and a methyl radical, and y can be zero or an integer of from one to twelve; and wherein n can be an integer of from one to five.

The present polymeric phosphoramidate polyols are used as correctants in polyurethane foam production. They are employed together with the conventional polyols used in polyurethane formulation in amounts sufficient to improve flame resistance of the polyurethane resin.

Any organic polyisocyanate can be advantageously employed. These include the conventional isocyanates as, for example, 80:20 mixture of 2,4- and 2,6-toluene diisocyanate isomers, diphenylmethane 4,4'-diisocyanate, hexamethylene diisocyanate, polymeric diphenylmethane diisocyanate and the like.

The polyurethane foams are prepared with conventional reaction catalysts, blowing agents, and surfactants.

The foams thus produced have excellent physical properties and flame resistance. Most important, these polyurethane foams contain bromine and phosphorus atoms which are chemically bound to the polymer chain, thus providing a permanent flame resistance to the polymer.

Since there are no hydrogen atoms in a position alpha to bromine atoms in the polymeric phosphoramidate polyols of the present invention, the usual degradation of the polymer initiated by a facile HBr elimination cannot occur, hence the foams have good light and heat stability. Thus, a serious disadvantage encountered in practice with bromine-containing flame retardants has been overcome with the novel compositions of this invention.

DESCRIPTION OF THE PREFERRED EMBODIMENTS

The spirocyclic phosphoramidites of formula I above employed as starting materials are conveniently prepared from a common intermediate 3,9-dichloro-2,4,8,10-tetraoxa-3,9-diphosphaspiro [5.5] undecane, intermediate (IV) below, which was first described by H. I. Lukas et al, J. Am Chem. Soc. 72, 5491 (1950).

The intermediate IV is allowed to react with an appropriate secondary amine yielding the spirocyclic phosphoramidite according to the equation:

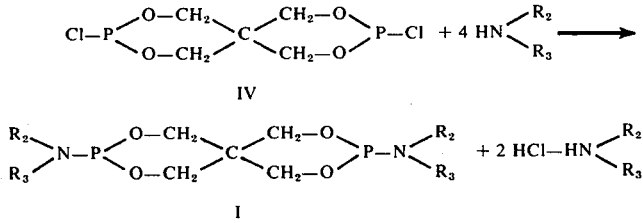

Usually four moles of the amine per mole of spirocyclic bisphosphorochloriadate (IV) are employed. Alternatively, two moles of a secondary amine and two moles of a tertiary amine, used as an acid acceptor, can be employed to produce spirocyclic phosphoramidites of formula I above. The latter method was described in U.S. Pat. No. 3,138,585 issued June 23, 1964 in the name of Ratz, which discloses the synthesis of 3,9-bis(1-aziridinyl)-2,4,8,10-tetraoxa-3,9-diphosphaspiro [5.5] undecane prepared from the intermediate IV and aziridine in presence of triethylamine as an acid acceptor.

A large variety of secondary amines can be employed advantageously in the synthesis of the spirocyclic phosphoramidites of formula I which are the starting materials for the production of the compositions of this invention. The type of secondary amines contemplated include alkyl, aryl, alkaryl and aralkyl amines. The two groups of a secondary amine can be the same or different. The alkyl groups can be straight chain or branched; the aryl groups can have substituents. Also included are cyclic secondary amines such as, for example, azetidine, pyrrolidine, piperidine, morpholine, and mono N-substituted piperazines. The preferred secondary amine is diethyl amine.

The spirocyclic phosphoramidites derived from primary amines and the intermediate IV are not useful in the production of the compositions of this invention because on treatment with bromine these primary phosphoramidites give intractable, amorphous, highly insoluble mixtures.

The primary amides of phosphorous acid esters can exist in two forms *a* and *b* which are in equilibrium [D. E. C. Cordridge, Topics in Phosphorus Chemistry, Vol. 6, p. 297, John Wiley & Sons (1969)].

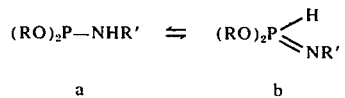

a      b

Thus both forms, *a* and *b*, can evidently interact with bromine, giving rise to a mixture of products. On the other hand, secondary phosphoramidites (derived from secondary amines) can exist only in one form, due to the absence of a labile hydrogen on the nitrogen atoms. Thus, treatment of secondary phosphoramidites of formula I with bromine results in a smooth, high-yield conversion to the Arbuzov type rearrangement products having formula II.

Bromine in a solvent, preferably chloroform, is added at atmospheric pressure to the spirocyclic phosphoramidite of structure I dissolved in a suitable solvent, such as chloroform, to provide a high yield of the bromine-containing amidophosphorobrominate characterized by structure II. The molar ratio of bromine to phosphoramidite is almost invariably approximately 2:1.

The Arbuzov type rearrangement is a strongly exothermic reaction so that stepwise bromine addition and external cooling are required to maintain the temperature of the reaction mixture in the desired range of 0°C. to −30°C. The amidophosphorobrominate intermediate II is substantially free of by-products and is thus conveniently prepared in situ for the subsequent step.

Stepwise addition of the intermediate II (prepared in situ) to an appropriate diol, in the presence of an acid acceptor such as a tertiary amine, leads to the phosphoramidate diol of formula III. The reaction mixture is normally refluxed for a few hours to ensure complete conversion.

The amine salt by-product is then removed by filtration and extraction with water. The organic phase is concentrated under reduced pressure to remove unreacted amine and diol, if any is present, yielding the product as a pot residue.

A wide range of inert organic solvents can be used advantageously in this reaction. It is preferable, but not essential, to select a solvent in which all reactants are soluble, especially the more insoluble diols. For example, benzene can be employed with triethylene glycol; chloroform with dipropylene glycol and 1,3-butanediol; and acetonitrile with ethylene glycol which is insoluble in the above mentioned solvents.

The molar ratios employed can vary from 1.5 moles to several moles excess (for example as much as 5 moles) of the diol per mole of the amide of formula I. The preferred ratio is approximately 2:1. When a large excess of the diol is used, the unreacted portion of the diol must be removed by distillation, generally under reduced pressure.

A great variety of diols can be employed in the preparation of novel compositions of this invention. Preferred diols include ethylene, diethylene, triethylene, propylene, dipropylene, and tripropylene glycols. Other diols contemplated for the production of compounds of this invention include aliphatic diols containing from 3 to 10 carbon atoms. These can be linear or branched, bearing either all primary or all secondary OH groups or a mixture of primary and secondary OH groups. The above described diols can also contain unsaturation or halogen substituents. Examples of such diols include 1,2-propanediol, 1,2-butanediol, 1,3-butanediol, 2-butenediol-1,4, 2-butynediol-1,4, 2,3-dibromo-1,4-butanediol, 2,3-dichloro-1,4-butanediol, 2,3-dibromo-2-butenediol-1,4, 3-bromo-1,2-propanediol, 3-chloro-1,2-propanediol, 2,2-bis(-bromomethyl)-1,3-propanediol, and 2,2-bis(chloromethyl)-1,3-propanediol, and the like.

Depending on the phosphoramidite and the diol employed, the polymeric bromine-containing phosphorus acid ester diols obtained are either oils or viscous resins. These polymers are soluble in polyols normally employed in polyurethane production. They are soluble in most common organic solvents as well. This is in agreement with analytical data which indicate that a substantial portion of the polymer consists of low molecular weight species, e.g., where *n* is an integer of from one to five.

The solubility of the polyols of the invention renders them especially useful in polyurethane foam production by the well-known "one-shot" method where homogeneity and low viscosity of the polyol component are desirable features.

Examples 1 through 7 illustrate the general procedure for the preparation of phosphoramidate polyols of the present invention. In no way should these specific examples be interpreted as limiting the scope of the present invention.

Examples 8 and 9 illustrate the utility of these phosphoramidate polyols as flame retardants for polyurethane resins.

EXAMPLE 1

Bromine (282 g., 1.76 moles) in chloroform (300 ml.) was added dropwise with stirring to a solution of 3,9-bis(diethylamino)-2,4,8,10-tetraoxa-3,9-diphosphaspiro[5.5]undecane (295 g., 0.87 mole) in chloroform (500 ml.). During addition the temperature of the solution was kept at about −30°C. by means of an acetone-dry ice bath. At the very end of addition the reaction solution acquired a permanent brownish color.

The resulting solution was then concentrated to about one-half volume under an aspirator pressure and added dropwise with stirring to the solution of dipropylene glycol (234 g., 1.75 moles) and triethylamine (180 g., 1.78 moles), in chloroform (800 ml.). causing a slow temperature rise to 45°C. The resulting solution was kept under reflux for two hours. On cooling some amine salt precipitated out of solution.

The mixture was washed twice with 500 ml. of water, dried over anhydrous sodium sulfate and concentrated first under an aspirator pressure and finally under 0.1–0.3 mm. pressure at 100°C. pot temperature.

The product (501.7 g.) was a brown oil neutral to moist litmus.

Analysis: OH Number 44.6, 9.86, 9.69% P; 25.66, 25.76% Br.

EXAMPLE 2

The procedure of Example 1 was repeated except that dipropylene glycol was replaced by diethylene glycol. Also in this reaction 4 moles (an excess) of the diol were employed per mole of the phosphoramidite.

The product obtained was a brown oil neutral to moist litmus.

Analysis: OH Number 82.7; 10.45% P; 24.71% Br.

EXAMPLE 3

The procedure of Example 1 was repeated except that dipropylene glycol was replaced by triethylene glycol and the reaction solvent employed was benzene.

The product was a brown oil neutral to moist litmus.

Analysis: OH Number 73.5; 8.80, 8.86% P; 25.97, 26.01% Br.

EXAMPLE 4

Bromine (131 g., 0.82 mole) in chloroform (200 ml.) was added dropwise with stirring to a solution of 3,9bis(diethylamino)-2,4,8,10-tetraoxa-3,9-diphosphaspiro[5.5] undecane (135 g., 0.40 mole) in chloroform (250 ml.). During addition the temperature of the reaction solution was kept at $-10°$ to $-20°C$. by means of an acetone-dry ice bath. At the very end of addition the solution acquired a permanent brownish color.

The resulting solution was then concentrated to about 250 ml. and added dropwise with stirring to the solution of 1,,2-propanediol (61.0 g., 0.80 mole) and triethylamine (81.0 g., 0.80 mole) in chloroform (400 ml.), causing a slow temperature rise to 40°C. The resulting solution was kept under reflux for two hours, then washed two 300 ml. portions of water and concentrated first under an aspirator pressure and finally under 0.1–0.3 mm. pressure at about 100°C. pot temperature.

The product (200 g.) was a brown viscous oil neutral to moist litmus.

Analysis: OH Number 92.7; 10.63, 10.74% P; 27.91, 28.03% Br.

EXAMPLE 5

Bromine (260 g., 1.62 moles) in chloroform (300 ml.) was added dropwise with stirring to a solution of 3,9-bis(diethylamino)-2,4,8,10-tetraoxa-3,9-diphosphaspiro[5.5] undecane (272.5 g., 0.81 mole). During addition the temperature of the solution was kept at $-20°$ to $30°C$. by means of an acetone-dry ice bath.

The resulting brownish solution was concentrated under an aspirator pressure, giving the Arbuzov rearrangement product as a light tan semi-crystalline waxy solid (517.8 g., 0.79 mole, 97% yield).

A portion of the product (266 g., 0.41 mole) was dissolved in anhydrous acetonitrile (250 ml.) and the resulting solution was then added dropwise with stirring to an excess of ethylene glycol (125 g., 2.0 moles) and triethylamine (90.0 g., 0.89 mole) in acetonitrile solution (400 ml.). A mild exotherm was observed and at the end of addition the temperature of the reaction solution reached about 50°C.

The resulting solution was concentrated under an aspirator pressure. The residue was diluted with chloroform (500 ml.) and then washed with two 250 ml. portions of water. The chloroform phase was dried over anhydrous sodium solfate and concentrated first under an aspirator pressure and finally under 0.5 mm. pressure at about 100°C. pot temperature.

The product was a brown oil (184 g.) neutral to moist litmus.

Analysis: OH Number 91.3; 10.42% P: 34.70, 33.90% Br.

EXAMPLE 6

Bromine (123 g., 0.77 mole) in chloroform (200 ml.) was added dropwise with stirring to a solution of 3,9-bis(piperidino)-2,4,8,10-tetraoxa-3,9-diphosphaspiro[5.5] undecane (139-g., 0.38 mole) in chloroform (300 ml.). During addition the temperature of the solution was kept at about 0°C. by means of an acetone-ice bath. At the very end of addition the reaction solution acquired a permanent brownish color.

The resulting solution was concentrated to about 250 ml. and added dropwise with stirring to a solution of 1,3-butanediol (69.4 g., 0.77 mole) and triethylamine (78.0 g., 0.79 mole) in chloroform (400 ml.), causing a slow temperature rise to 55°C. The reaction solution was kept under reflux for two hours, then washed with water (2 × 300 ml.), dried over anhydrous sodium sulfate, and concentrated first under an aspirator pressure and finally under 0.1–0.3 mm. pressure of Hg at about 100°C pot temperature.

The resulting product was a brown viscous oil neutral to moist litmus.

Analysis: OH Number 99.7; 10.91% P; 27.8, 28.0% Br.

EXAMPLE 7

Bromine (152 g., 0.95 mole) in chloroform (200 ml.) was added dropwise with stirring to a solution of 3,9-bis(N-methylanilino)-2,4,8,10-tetraoxa-3,9-diphosphaspiro[5.5] undecane (192 g., 0.47 mole) in chloroform (400 ml.). During addition the temperature of the solution was kept at $-10°$ to $-20°C$. by means of an acetone-dry ice bath. At the very end of addition the reaction solution acquired a permanent brownish color.

The resulting solution was concentrated to about 250 ml. and added dropwise with stirring to a solution of 1,2-propanediol (68.5 g., 0.90 mole) and triethylamine (101 g., 1.0 mole) in chloroform (400 ml.), causing slow temperature rise to about 50°C. The reaction solution was kept under reflux for two hours, then washed with water (2 × 300 ml.), dried over anhydrous sodium sulfate, and concentrated first under an aspirator pressure and finally under 0.1–0.3 mm. pressusre at about 100°C. pot temperature.

The resulting product was a brown oil neutral to moist litmus.

Analysis: OH Number 47.6; 9.61, 9.7% P; 23.42, 23.32% Br.

The following table indicates the structures of R and $R_1$ in the products of examples 1 through 7:

| Example Number | R | $R_1$(Diol Residue) |
|---|---|---|
| 1 | Diethylamino | $-\underset{CH_3}{CHCH_2}-O-CH_2\underset{CH_3}{CH}-$ |

-continued

| Example Number | R | R₁(Diol Residue) |
|---|---|---|
| 2 | " | —CHCH₂—O—CH₂—CH₂— |
| 3 | " | —CH₂CH₂—O—CH₂CH₂—O—CH₂—CH₂— |
| 4 | " | —CH₂C(H)(CH₃)— |
| 5 | " | —CH₂CH₂— |
| 6 | Piperidino | —CH₂CH₂C(H)(CH₃)— |
| 7 | N-methylanilino | —CH₂C(H)(CH₃)— |

The phosphoramidate diols of the invention can be employed together with other known polyols as co-reactants with polyisocyanates, especially diisocyanates, in the production of polyurethanes, as is illustrated by Examples 8 and 9. Generally the phosphoramidate diols of the invention will have an average hydroxyl number of from 35 to 100, a phosphorus content of between 5 and 20% by weight, and a bromine content of from 10 to 50% by weight.

EXAMPLE 8

This example illustrates the utility of the novel phosphoramidate polyols of this invention in the production of flame-retarded rigid type polyurethane foams.

A fluorocarbon blowing agent (45 g.) ("Freon F11" (trademark)) and a silicone surfactant (1.0 g.) (DC-193 (trademark)) were added to a solution of an alkanolamine based polyol ("Rubicol R-350-X" (trademark)) having an OH Number of 520, a sorbitol-based polyol (30 g.) ("Rubicol RS-700" (trademark)) having an OH Number of 492, and phosphoramidate polyol (15 g.) having an OH Number of 91, prepared as described in Example 5.

The ingredients were thoroughly mixed and combined with diphenylmethane diisocyanate (108 g.). The reaction mixture had a 30–34 second cream time and a 1 minute and 15 second rise time.

The resultant rigid foam thus produced was rated as non-burning by the ASTM D-1692-59T flammability test. That is, after a 1-inch length of the sample was consumed, the flame source was withdrawn and the flame extinguished itself immediately.

Another foam was prepared as described above except that the phosphoramidate polycol of Example 5 was replaced with that prepared according to the procedure of Example 2. The foam had a 30-35 sec. cream time and a 1 min. 7 sec. rise time. It was also rated as non-burning by the ASTM D-1692-59T flammability test.

EXAMPLE 9

This example illustrates the utility of the novel compositions of this invention in the production of flame retarded flexible polyurethane foams.

Stannous octoate (0.3 g.) ("T-9"(trademark)catalyst), an amine type catalyst (0.29 g.)("Dabco 33-LV"(trademark)), a silicone type surfactant (4.0 g.) ("L-520"(trademark)), and water (3.5 g.) were combined with a solution consisting of a polyether polyol ("1446 Polyol" (trademark)) having a molecular weight of about 3500 (77.4 g., OH Number 48.5) and the phosphoroamidate polyol (22.6 g.) prepared as described in Example 4, having an OH number of 92.7).

The resulting mixture was thoroughly mixed and combined with toluene diisocyanate (42.9 g., and 80:20 mixture of 2,4- and 2,6-isomers). The resulting foam was subjected to a 10-min. post cure cycle at 100°C. A foam having fine open cells and excellent resilience was obtained.

The foam was rated as self-extinguishing according to the ASTM D-1692-59T Flammability test. The foam prepared without the phosphoramide polyol was rated as burning by the same test.

GENERAL

Since the chemical compounds of Formula II above are new and novel, claims to these compounds per se as well as to their use as intermediates for making the co-reactive chemicals of Formula III above.

I claim:

1. A polymeric bromine-containing phosphoramidate polyol having the structure

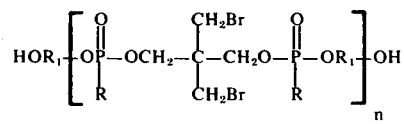

wherein R is a radical having the formula —NR₂R₃ wherein R₂ and R₃ can be the same or different and are alkyl radicals having from 1 to 6 carbon atoms, phenyl or aralkyl or alkaryl radicals having from seven to twelve carbons atoms; R₁ is a diradical selected from —CH₂CH₂—, —CH(CH₃)CH₂—, —CH(CH₃)CH₂CH₂—, —CH₂CH=CHCH₂—, —CH₂C≡CCH₂—, —CH(CH₂Br)CH₂—, —CH(CH₂Cl)CH₂—, —CH₂C(CH₂Br)₂CH₂—, —CH₂C(CH₂Cl)₂—, —CH₂CH₂—O—CH₂CH₂—, —CH₂CH₂—O—CH₂C-

H₂—O—CH₂CH₂— and —CH(CH₃)C-
H₂—O—CH₂CH(CH₃)—; and n is an integer of from 1 to 5.

2. The phosphoramidate polyol of claim 1 wherein R is selected from the group consisting of methylanilino and diethylamino, and R₁ is selected from the group consisting of —CH₂CH₂—, —CH(CH₃)CH₂—, —CH₂CH₂—O—CH₂CH₂—, —CH(CH₃)C-H₂—O—CH₂CH(CH₃)— and —CH₂CH₂—O—CH₂C-H₂—O—CH₂CH₂—.

3. A polymeric bromine-containing phosphoramidate polyol having the structure:

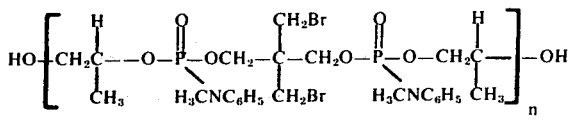

wherein n is an integer of from 1 to 5.

4. A polymeric bromine-containing phosphoramidate polyol having the structure:

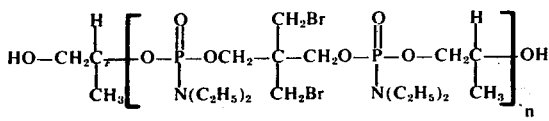

wherein n is an integer of from 1 to 5.

* * * * *

UNITED STATES PATENT OFFICE
CERTIFICATE OF CORRECTION

PATENT NO. : 3,932,565
DATED : Jan. 13, 1976
INVENTOR(S) : Wadim Batorewicz

It is certified that error appears in the above-identified patent and that said Letters Patent are hereby corrected as shown below:

Col. 10, line 65: delete "-CH$_2$C CCH$_2$-," and substitute -- -CH$_2$C≡CCH$_2$-, -- therefor.

Col. 10, line 67: delete "-CH$_2$C(CH$_2$Cl)$_2$-," and substitute -- -CH$_2$C(CH$_2$Cl)$_2$CH$_2$-, -- therefor.

Col. 12, lines 1-5: delete " HO-[-CH$_2$C(H)(CH$_3$)--O-] " and substitute -- HO-CH$_2$C(H)(CH$_3$)--[O-] -- therefor.

Signed and Sealed this

Thirty-first Day of August 1976

[SEAL]

Attest:

RUTH C. MASON
Attesting Officer

C. MARSHALL DANN
Commissioner of Patents and Trademarks